(12) United States Patent
Brass et al.

(10) Patent No.: US 8,016,120 B2
(45) Date of Patent: Sep. 13, 2011

(54) METHOD FOR PURIFYING A VIRAL SUSPENSION

(75) Inventors: Olivier Brass, Caluire-et-Cuire (FR); Jean-Marc Contzen, Poses (FR); Alain Francon, Bessenay (FR); Michel Tardy, Lyons (FR)

(73) Assignee: Sanofi Pasteur SA, Lyons (FR)

( * ) Notice: Subject to any disclaimer, the term of this patent is extended or adjusted under 35 U.S.C. 154(b) by 380 days.

(21) Appl. No.: 12/145,931

(22) Filed: Jun. 25, 2008

(65) Prior Publication Data

US 2009/0023197 A1 Jan. 22, 2009

Related U.S. Application Data

(60) Provisional application No. 60/990,101, filed on Nov. 26, 2007.

(30) Foreign Application Priority Data

Jun. 27, 2007 (FR) .................... 07 04607

(51) Int. Cl.
*B04B 5/06* (2006.01)
*B01D 24/32* (2006.01)
*B01D 33/00* (2006.01)

(52) U.S. Cl. .................. 210/360.1; 210/380.1; 494/22; 494/37

(58) Field of Classification Search ............ None
See application file for complete search history.

(56) References Cited

U.S. PATENT DOCUMENTS

| 4,158,054 A | 6/1979 | Furminger et al. |
| 6,146,874 A | 11/2000 | Zolotukhin et al. |

FOREIGN PATENT DOCUMENTS

| WO | WO 03/045568 A1 | 6/2003 |
| WO | WO 2007/067736 A2 | 6/2007 |

OTHER PUBLICATIONS

Gschwender, et al. Lymphocytic Choriomeningitis Virus I. Concentration and Purification of the Infectious Virus. J Virol. 1975; 15(6): 1317-1322.*
Hilfenhaus, et al. Large-scale purification of animal viruses in the RK-model zonal ultracentrifuge: II. Influenza, mumps and Newcastle disease viruses. J. Biol. Stand. 1976; 4(4): 273-283.*
Reimer, et al. (Purification of Large Quantities of Influenza Virus by Density Gradient Centrifugation. J. Virol. 1967; 1(6): 1207-1216).*
Dorin and Cummings (Beckman Coulter Technical bulletin T-1780B, 2004).*
Peng H.H. et al.: "A rapid and efficient method ofr purification of recombinant adenovirus with arginine-glycine-aspartic acid-modified fibers," Science direct—Analytical Biochemistry 354 (2006), pp. 140-147.

(Continued)

*Primary Examiner* — Zachariah Lucas
*Assistant Examiner* — Stuart W Snyder
(74) *Attorney, Agent, or Firm* — McDonnell Boehnen Hulbert & Berghoff LLP

(57) ABSTRACT

The invention relates to a method for obtaining viruses from a liquid viral suspension, according to which:
the viral suspension is subjected to density gradient ultracentrifugation,
the ultracentrifugation is carried out continuously, and
the density gradient is a discontinuous gradient comprising at least 2 steps.

4 Claims, 1 Drawing Sheet

OTHER PUBLICATIONS

Reimer, C. B. et al.: "Purification of Large Quantities of Influenza Virus by Density Gradient Centrifugation," Journal of Virology, Dec. 1967, vol. 1, No. 6, pp. 1207-1216.

Heinz, F. X. et al.: "Preparation of a Highly Purified Vaccine Against Tick-Borne Encephalitis by Continuous Flow Zonal Ultracentrifugation," Journal of Medical Virology, vol. 6, No. 3, 1980, pp. 213-222.

Kumar, Ananda Arone Prem et al.: "Process Standardization for Optimal Virus Recovery and Removal of Substrate DNA and Bovine Serum Proteins in Vero Cell-Derived Rabies Vaccine," Journal of Bioscience and Bioengineering, vol. 94, No. 5, pp. 375-383.

Dorin, M. et al.: "Principles of Continuous Flow Centrifugation," Article Internet, [Online] XP002452568; Extrait de l'Internet: URL:http://www.beckmancoulter.com/vsearch/parametric.asp?QueryText=continuous+flow&formSubmitted=1&QuerySubmit=true> [extrait le Jun. 1, 2007].

Anonyme: "KII & PKII Ultracentrifuge Systems Solutions for Process Development to Industrial Scale Manufacturing," Article internet, [Online] XP002452569; Extrait de l'Internet: URL:http://www.awst.com/documents/AWST_ProdcutBroch.pdf> [extrait le May 1, 2007].

* cited by examiner

METHOD FOR PURIFYING A VIRAL SUSPENSION

CROSS REFERENCE TO RELATED APPLICATIONS

This application claims the benefit of the filing date, under 35 USC §119(e), of U.S. Provisional Application Ser. No. 60/990,101, filed Nov. 26, 2007, the disclosure of which is incorporated herein by reference in its entirety.

BACKGROUND OF THE INVENTION

1. Field of the Invention

The present invention relates to the field of viral purification, in particular to a method for obtaining viruses from a liquid viral suspension.

2. Summary of the Related Art

Methods for purifying viral suspensions are known in the pharmaceutical field, and in particular in the vaccines field.

Thus, patent FR2201079 describes, in particular, a method for purifying viruses from a viral suspension which is introduced into a zonal centrifuge rotor while it is stopped; after the rotor has begun to slowly rotate (between 2000 and 5000 rpm), at least 2 cushions of liquid of different density are introduced at the periphery of the rotor; then, once the rotor is filled with the liquid to be treated, said rotor is accelerated to a speed sufficient to separate the viruses from the impurities and, finally, after the speed of the rotor has been brought back to between 2000 and 5000 rpm, a liquid of density equal to or greater than the content of the rotor is introduced by the periphery, in order to empty the rotor by its central channel; and the fractions containing the virus freed of the impurities is subsequently collected.

During rotation, the cushions of different density are converted by diffusion into a nonlinear gradient.

The method described in said patent, which is a discontinuous method, has however the drawback of making it possible to process only constant and limited volumes of viral suspension, and therefore of making it necessary to pre-concentrate the viral suspension to be purified and/or to reproduce the same procedures several times in order to process a large volume of liquid.

The fact of using such a method also complicates attempts to have a process which is carried out entirely under sterile conditions.

SUMMARY OF THE INVENTION

A subject of the present invention is a method for obtaining viruses from a liquid viral suspension, according to which the viral suspension is subjected to density gradient ultracentrifugation, wherein,
the ultracentrifugation is carried out continuously,
the density gradient is a discontinuous gradient comprising at least 2 steps.

Thus, it is possible to integrate this purification step into an on-line manufacturing process, thereby making it possible to reduce the risks of contamination and allowing automation which is advantageous from an industrial point of view.

DETAILED DESCRIPTION OF THE INVENTION

According to a specific characteristic of the method of the invention, the centrifugal force to which the viral suspension is subjected at the inlet of the ultracentrifuge is between 36 000 and 60 000 g, and that which exists at the periphery is between 90,000 and 120,000 g.

Thus, the viruses can optimally penetrate the density gradient layer, whereas the unwanted elements of the viral suspension directly cross the ultracentrifuge and are eliminated, without being able to penetrate the gradient, or else penetrate the gradient but migrate very little.

According to another specific characteristic of the method according to the invention, the density gradient is a sucrose step gradient, obtained by superimposing at least 2 layers of sucrose of different density, and a layer of buffer solution.

At least 2 well-differentiated steps corresponding to "jumps" in density, which allow good separation of the constituents of the viral suspension, are thus obtained.

Many advantages of the invention will emerge upon reading the detailed description hereinafter, with reference to the figures which represent schematically a device for the implementation thereof.

An example of an ultracentrifugation device which is particularly suitable for the implementation of the invention is a device such as that described in patent application US 2005/0215410.

As appears in the figures, such a device consists mainly of a rotor comprising a cylindrical outer shell 1 constituting a tank which has a central core 2. The tank has, in its lower part, an inlet 3 for the liquid to be treated and, in its upper part, an outlet 4. In the interests of simplicity, the driving means and the means of attachment of the various parts of the device have not been represented.

Figure 1:
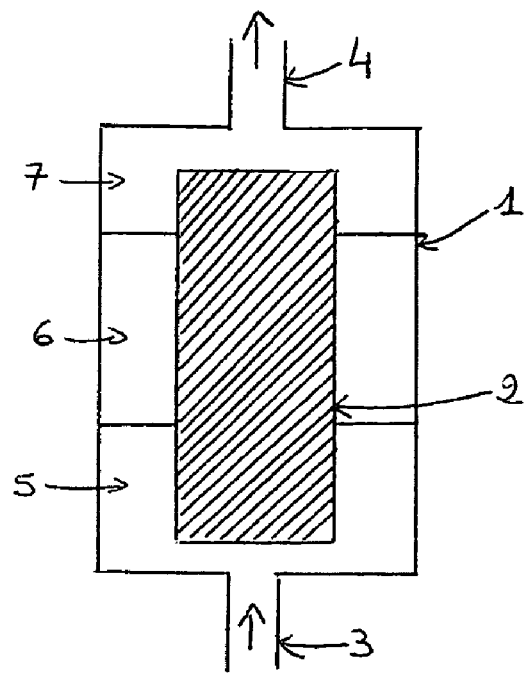
FIG. 1 is, schematically, a device for implementation of the invention, while stopped.
Figure 2:
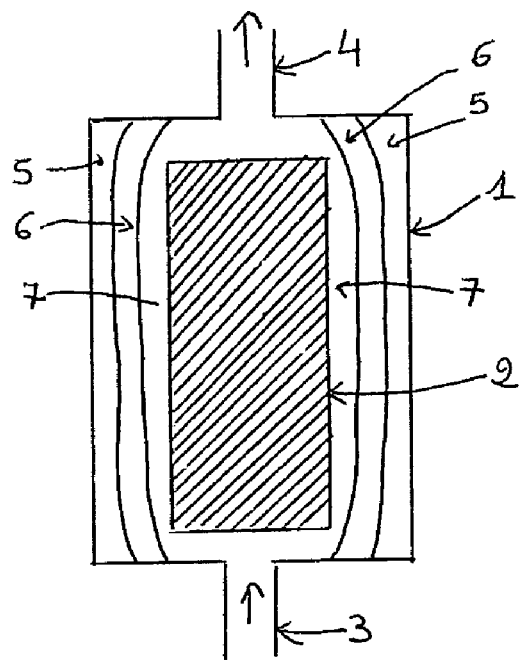
FIG. 2 is, schematically, a device for implementation of the invention, while operating.

The volume available between the outer shell 1 and the core 2 is taken up by a density gradient consisting, according to the invention, of at least 2 layers, 5 and 6, of different density, and of a layer 7 of buffer solution. When the device is stopped, the layers of the density gradient are superimposed horizontally, as is shown in FIG. 1, the layer of highest density being underneath and the layer of buffer being on the top. When the device is being used, as is shown in FIG. 2, the layers of different density become organized concentrically around the core, the layer of highest density being the further from the core, whereas the viral suspension to be treated, which enters by the inlet 3, circulates in the zone close to the core, before being evacuated via the outlet 4.

In one aspect, the invention comprises a device for the implementation of the method as described herein, comprising:
a rotor capable of reaching a rotational speed of at least 35 000 rpm, comprising a titanium-walled cylindrical tank and a ribbed inner core made of a PPE resins comprising an amorphous blend of PPO polyphenylene ether resin and polystyrene, such as NORYL™,
an inlet for the viral suspension to be treated,
an outlet for the treated liquid
wherein the volume available for the density gradient and the circulation of the liquid to be treated is approximately 8 liters.

When using the apparatus according to the invention, the density gradient will generally consist of at least 2 layers of sucrose of different density, and one layer consisting of a buffer solution.

According to the invention, the viral suspension that is treated is a liquid suspension that contains viruses which may or may not be live. They may be viruses used in the manufacture of vaccines, and in particular flu, measles, mumps, herpes, yellow fever, rabies or polio viruses or any other virus having characteristics that allow it to be used for the prevention of diseases. These viruses may have been produced by culturing on cells, or on organs, or, as is for example the case with the flu virus, on eggs. In the case of virus production on cells, the principal elements to be eliminated will be the proteins and the cellular DNA. In the case of production on eggs, one of the elements that it is advisable to eliminate is the ovalbumin. In fact, the standards established by the health authorities in Europe set a limiting threshold of 1 µg of ovalbumin per dose of vaccine administered. Of course, industrial companies endeavor to fall well below the authorized threshold; it is therefore important to be able to provide a simple and effective method which makes it possible to reduce by a maximum the impurities originating from the virus production.

The method according to the invention is of very specific advantage and has been found to be highly effective when the viral suspension to be treated consists of allantoic fluid comprising flu virus that it is advisable to separate from the ovalbumin originating from the eggs used for the viral propagation.

The method according to the invention is carried out in a single zonal ultracentrifugation step. To this end, the ultracentrifugation tank used is a cylindrical tank whose walls are preferably made of titanium; it has, at its center, a cylindrical core with grooves that allow liquid to flow; this core is advantageously made of NORYL™. The volume available between the core and the outer walls is, according to the invention, sufficient to introduce a product that allows an at least 2-step density gradient. Thus, it has been noted that, by using an ultracentrifugation system of KII type with a K10 core, a volume of 8 liters perfectly suitable for the invention is obtained.

In order to provide the purification by density gradient, at least 3 layers of different density are loaded into the ultracentrifuge tank while stopped. This density gradient can be obtained using various products such as sucrose, cesium chloride, potassium tartrate or potassium bromide, for example; particularly good results have been obtained with sucrose. It is thus possible to have 3 layers, 2 of the layers consisting of sucrose at different concentrations, and one of the layers consisting of a buffer solution. Depending on the nature of the viral suspension to be purified, it is possible to envision more layers, which will make it possible to have more steps of different densities.

The loading is carried out by first of all introducing the buffer liquid, and then the cushions in order of increasing density; this loading is carried out while the rotor is stopped.

When the loading is complete, the rotor is accelerated to its maximum speed, i.e. between 35 000 and 40 500 rpm. During the acceleration, the viral suspension to be treated is introduced via the inlet 3. The liquid to be treated then flows, as is shown in FIG. 2, along the core 2; at this site, it is subjected to a centrifugal force of between 36 000 and 60 000 g, whereas the acceleration in proximity to the outer wall is between 90 000 and 120 000 g; despite the relatively low centrifugal force to which the liquid to be treated is subjected at its entry into the ultracentrifuge, the virus can penetrate inside the gradient, and what was feared, too great a loss of virus, is not observed. Some of the unwanted proteins or particles also penetrate inside the gradient; however, the different density steps will constitute obstacles that some of the elements present at the beginning in the viral suspension cannot overcome. Since viruses are heavy particles, they themselves will migrate to their point of isodensity which is close to the end of the gradient. According to the invention, very good virus/ovalbumin is obtained. A 99% elimination of ovalbumin was thus obtained by means of a single ultracentrifugation step.

After the entire volume of viral suspension has been treated, the liquid of the density gradient is recovered in fractions of various densities and is treated in order to isolate the viruses from the most dense fractions.

The viruses can then be inactivated or treated in the usual manner.

The present invention makes it possible, surprisingly, to conserve the steps of the density gradient despite the high acceleration and the duration of this acceleration. The inventors had in fact feared that a volume as large as one of 8 l would result in instability of the gradient and that there would also be considerable loss of virus due to the speed of rotation at the inlet of the device being reduced compared with that which is customary practice in the prior art.

EXAMPLE

Purification of Flu Viruses From Egg Allantoic Fluid

An ultracentrifugation system of KII type is provided, having at its center a K10 core provided by Alfa Wasserman.

The following are successively introduced into the rotor, while stopped:
  slightly more than 8 l of 125 mM citrate buffer,
  3.4 l of a 34% sucrose solution, which displaces part of the citrate buffer,
  1.6 l of a 55% sucrose solution, which also displaces part of the citrate buffer.

The rotor is then accelerated up to a speed of 35 000 rpm, and the allantoic fluid to be treated, i.e. 60 liters, is introduced with a flow rate of 10 liters/hour. This allantoic fluid has been clarified and concentrated beforehand in order to eliminate some of the contaminants; it contains flu virus that it is desired to isolate in order to introduce it into a vaccine.

The ultracentrifugation is carried out for a period of 6 hours and then rinsing is carried out for 1 hour, replacing the allantoic fluid with 125 mM citrate buffer. This rinsing phase makes it possible not only to eliminate the impurities at the inlet of the gradient, but also and especially gives the virus more time to migrate in its isodensity zone.

After all the liquid to be treated has been ultracentrifuged, the rotation is stopped and the gradient is harvested in 32 fractions of 250 ml.

These fractions are then analyzed by refractive index, optical density and albumin assay, in particular. It is observed that very good virus/albumin separation resolution is obtained. The fractions comprising between 47% and 35% of sucrose, which are the fractions comprising the maximum of virus and the minimum of ovalbumin, are kept.

These fractions are then combined and standardized by dilution to constant optical density values indicative of the content of viral protein, before being fractionated and then inactivated and filtered so as to obtain a suspension of split inactivated viral particles.

It is observed that the viruses purified according to the method of the present invention are, before fragmentation, whole viruses, and that the concentration of ovalbumin in the harvested fractions is sufficiently low for subsequent use of these viruses in vaccine doses, observing the specifications of the European Pharmacopeia which requires an amount of ovalbumin of less than 1 µg/dose.

What is claimed is:

1. A method for obtaining viruses from a liquid viral suspension, the method comprising subjecting the viral suspension to density gradient ultracentrifugation, wherein, the ultracentrifugation is carried out continuously, and the density gradient is a discontinuous gradient comprising at least 2 steps wherein (i) the centrifugal force to which the liquid viral suspension is subjected at the inlet of the ultracentrifuge has a value of between 36 000 and 60 000 g, (ii) the centrifugal force to which the viral suspension is subjected at the end of the density gradient has a value of between 90 000 and 120 000 g, (iii) the volume available for the circulation of the liquid and the density gradient inside the ultracentrifuge is approximately 8 1, and (iv) the liquid viral suspension comprises flu virus and ovalbumin in suspension in concentrated allantoic fluid from eggs; and the virus-containing portion of the gradient is collected.

2. The method according to claim 1, wherein the density gradient is a sucrose gradient obtained by superimposing at least 2 layers of sucrose solutions of different density, and one layer of buffer solution.

3. The method according to claim 1, wherein the flow rate of the viral suspension in the ultracentrifuge is approximately 10 liters/hour.

4. The method according to claim 2, further comprising:

after all the viral suspension has been ultracentrifuged, recovering the sucrose solution present in the ultracentrifuge by fractions of increasing or decreasing density, retaining the fractions that comprise the virus.

* * * * *